US00PP34928P2

(12) United States Plant Patent
Avent

(10) Patent No.: US PP34,928 P2
(45) Date of Patent: Jan. 17, 2023

(54) ***PHLOX* PLANT NAMED 'BLUE RIBBONS'**

(50) Latin Name: *Phlox divaricata*
Varietal Denomination: Blue Ribbons

(71) Applicant: Tony Avent, Raleigh, NC (US)

(72) Inventor: Tony Avent, Raleigh, NC (US)

( * ) Notice: Subject to any disclaimer, the term of this patent is extended or adjusted under 35 U.S.C. 154(b) by 0 days.

(21) Appl. No.: 17/715,333

(22) Filed: Apr. 7, 2022

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 6/70
See application file for complete search history.

*Primary Examiner* — Anne Marie Grunberg
(74) *Attorney, Agent, or Firm* — Penny J. Aguirre

(57) ABSTRACT

A new cultivar of *Phlox* plant named 'Blue Ribbons' that is characterized by its variegated foliage with dark green centers and light green margins, its narrow leaves, its flowers that are violet-blue in color, and its fragrant flowers.

3 Drawing Sheets

Botanical classification: *Phlox divaricata.*
Cultivar designation: 'Blue Ribbons'.

CROSS-REFERENCE TO A RELATED APPLICATION

This application claims priority to European Community Plant Variety Office (CPVO) Plant Breeder's Rights Application No. 2021/3139 filed on Dec. 3, 2021, under 35 U.S.C. 119(f), the entire contents of which is incorporated by reference herein.

BACKGROUND OF THE INVENTION

The present invention relates to a new and distinct cultivar of *Phlox paniculata* and will be referred to hereafter by its cultivar name, 'Blue Ribbons'. 'Blue Ribbons' represents a new evergreen perennial grown for landscape use.

'Blue Ribbons' was discovered by the Inventor as a naturally occurring branch mutation of a seedling of an unnamed and unpatented plant of *Phlox divaricata* that was grown in a trial garden in Raleigh, N.C. in April of 2016.

Asexual propagation of the new cultivar was first accomplished by stem cuttings by the Inventor in November of 2017 in Raleigh, N.C. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Blue Ribbons' as a unique cultivar of *Phlox*.

1. 'Blue Ribbons' exhibits variegated foliage with dark green centers and light green margins.
2. 'Blue Ribbons' exhibits narrow leaves.
3. 'Blue Ribbons' exhibits flowers that are violet-blue in color.
4. 'Blue Ribbons' exhibits fragrant flowers.

The parent plant of 'Blue Ribbons' differs from 'Blue Ribbons' in having non-variegated foliage. 'Blue Ribbons' can be compared to *Phlox divaricata* cultivars 'Lemon Slice' (not patented), 'Dirigo Ice' (not patented) and 'Fuller's White' (not patented). 'Lemon Slice' is similar to 'Blue Ribbons' in having variegated foliage but differs from 'Blue Ribbons' in having foliage that is dark green in color with centers or mottling of lighter green and variegation that is highly variable and unstable. 'Dirigo Ice' differs from 'Blue Ribbons' in having flowers that are pale blue in color, non-variegated foliage, and a less vigorous growth habit. 'Fuller's White' differs from 'Blue Ribbons' in having flowers that are white in color, non-variegated foliage, and in having a very slow growth rate in the garden.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Plant Delights Nursery.

BRIEF DESCRIPTION OF THE DRAWINGS

The accompanying color photographs illustrate the overall appearance and distinct characteristics of the new *Phlox*. The photographs were taken of a 1.5-year-old plant of 'Blue Ribbons' as grown outdoors in a 23-cm container in Waddinxveen, The Netherlands.

The photograph in FIG.1 is a view of a plant of 'Blue Ribbons' in bloom.

Figure 1:
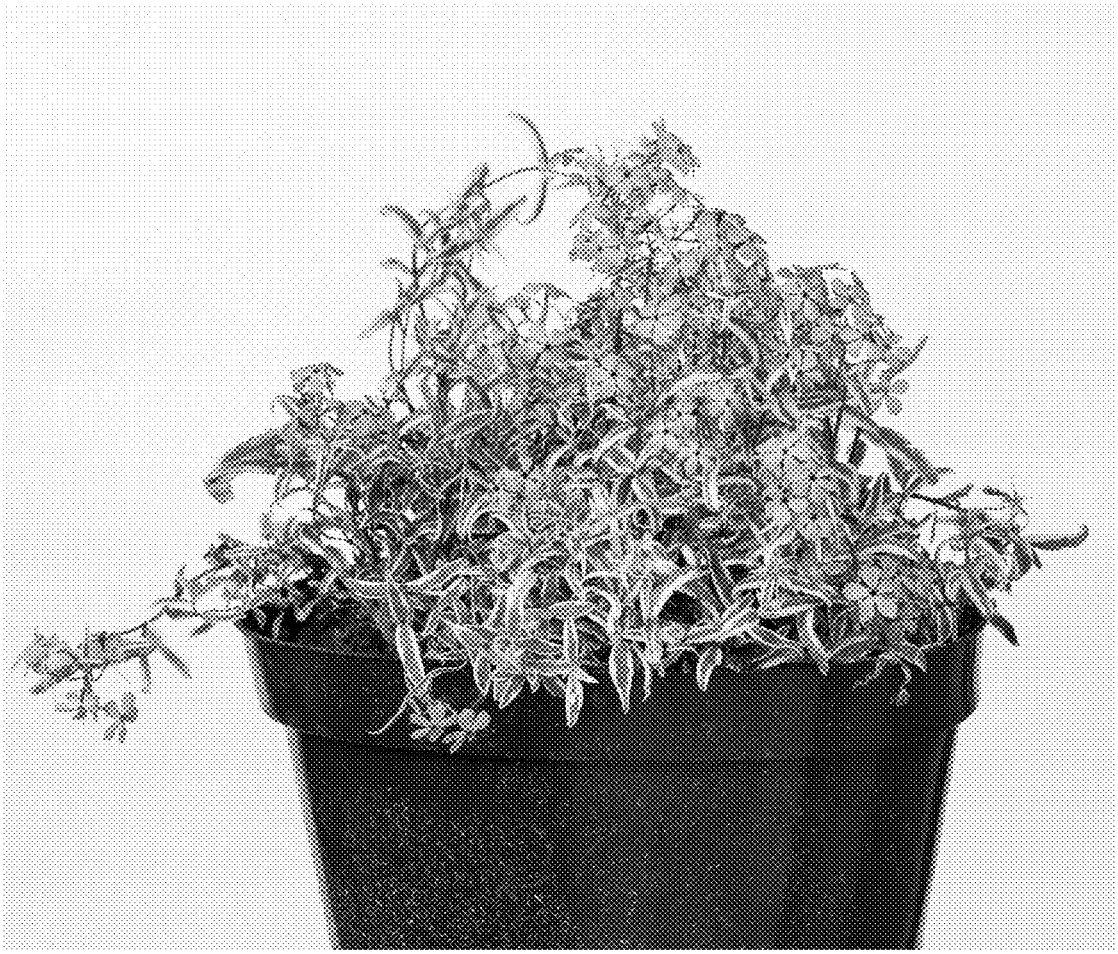
Figure 2:
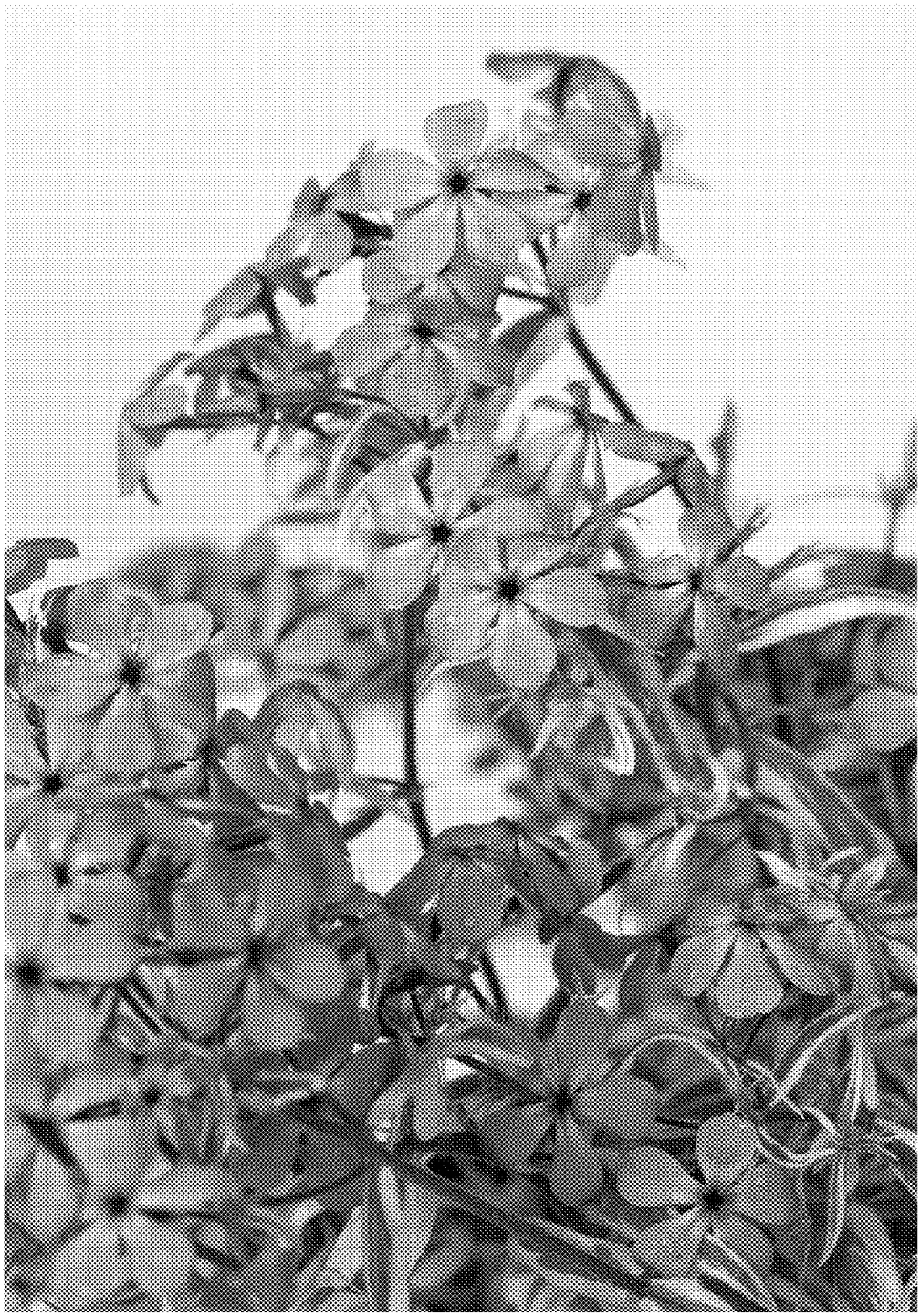

The photograph in FIG. 2 is a close-up view of the flowers of 'Blue Ribbons'.

Figure 3:
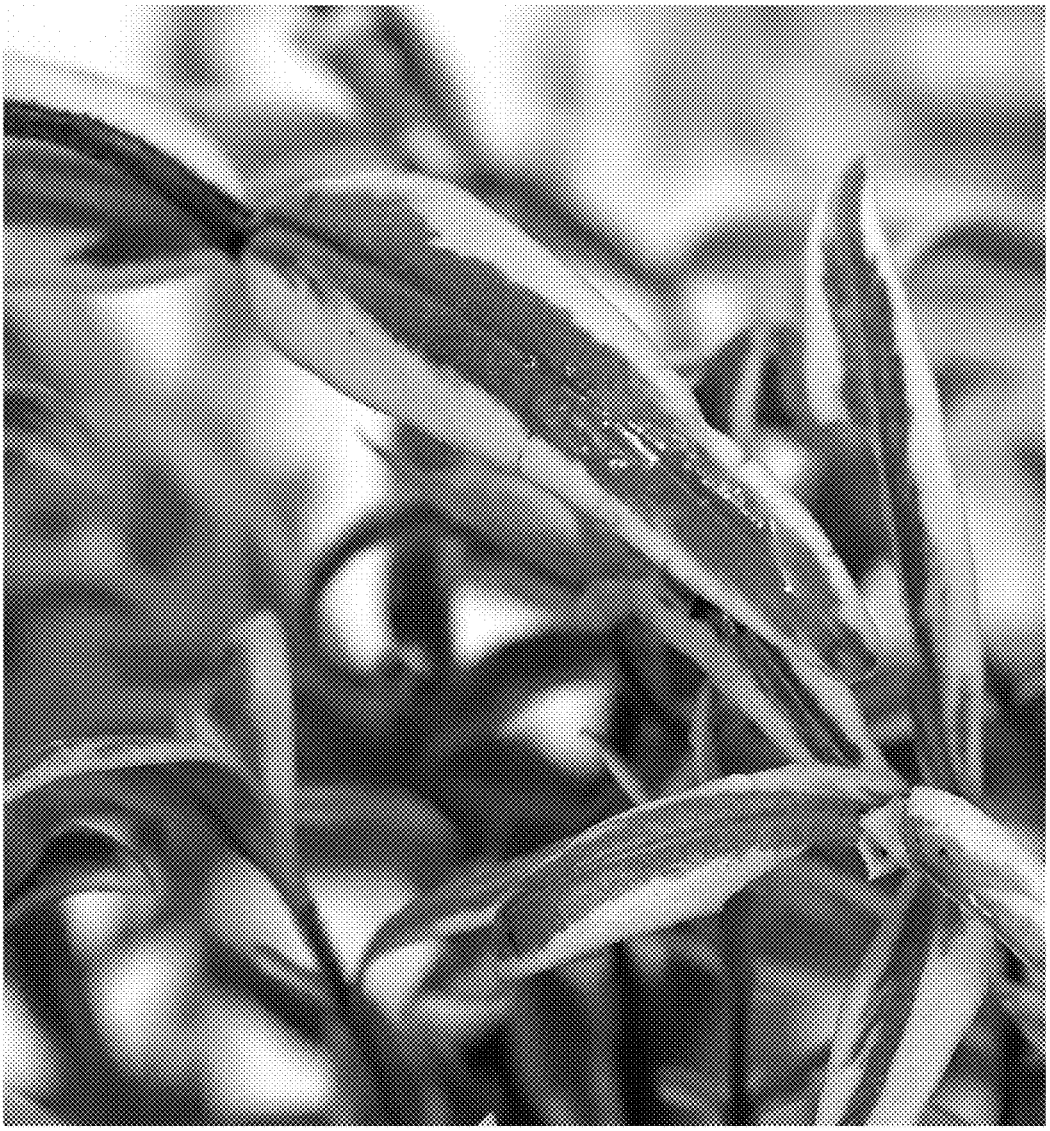

The photograph in FIG. 3 provides a close-up view of the foliage of 'Blue Ribbons'.

The colors in the photographs may differ slightly from the color values cited in the detailed botanical description, which accurately describe the colors of the new *Phlox*.

DETAILED BOTANICAL DESCRIPTION OF THE PLANT

The following is a detailed description of 1.5-year-old plants of the new cultivar as grown outdoors in 27-cm containers in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Spring, from March to mid-April in North Carolina.

*Plant type.*—Evergreen or semi-evergreen perennial (depending on location grown).

*Plant habit.*—Upright, broadly spreading, overall flattened shape.

*Height and spread.*—21.5 cm (soil level to top of foliar plane), 24 cm (soil level to top of floral plane), 24 cm in spread.

*Cold hardiness.*—U.S.D.A. Zones 4 to 10.

*Diseases and pests.*—No susceptibility or resistance to diseases or pest has been observed.

*Root description.*—Moderately fibrous, average diameter of roots is 2 mm, freely branched, moderately dense, smooth and glabrous surface, 156B to 156C in color, shallow to medium distribution in the soil.

*Root development.*—7 to 10 days for root initiation with IBA 3 treatment, 6 to 9 weeks from a rooted cutting to fully develop in a 1.5-liter container.

*Propagation.*—Stem cuttings.

*Growth rate.*—Moderate to highly vigorous.

Stem description:

*Stem size.*—An average of 22.6 cm in length, 1.75 mm in diameter.

*Stem shape.*—Round.

*Stem strength.*—Strong.

*Stem color.*—Young; 176B, tinged 145B, mature; 146A to 146B.

*Stem surface.*—Slightly glossy, surface densely covered with short soft pubescent hairs, an average of 0.8 mm in length, 156D in color.

*Stem aspect.*—Held in an average angle of 40° (varying between 0° and 80°).

*Internode length.*—An average of 2.7 cm.

*Branching habit.*—Freely branching, per plant; an average of 60 main branches, 200 lateral branches.

Foliage description:

*Leaf shape.*—Lanceolate.

*Leaf division.*—Simple.

*Leaf base.*—Rounded.

*Leaf apex.*—Acute.

*Leaf venation.*—Pinnate, color upper surface 152D, color lower surface 147C.

*Leaf margins.*—Entire, slightly revolute.

*Leaf attachment.*—Sessile.

*Leaf arrangement.*—Opposite.

*Leaf surface.*—Both surfaces very slightly glossy and sparsely to moderately covered with short pubescent hairs an average of 0.5 mm in length and too small to measure color.

*Leaf color.*—Young upper surface; 137D, margins are broad and irregular (variegated) 151D and 154B, young lower surface; 138A, margins are broad and irregular (variegated) ranging between 151D, 154A and 154B, mature upper surface; 137A and 137B, margins are broad and irregular (variegated) ranging between 144B, N144A, 150B, and 150C, mature lower surface; 137A and 137B, margins are broad and irregular (variegated) ranging between 144C, N144A and 154A to 154C.

*Leaf size.*—An average of 3.9 cm in length and 9.5 mm in width.

*Leaf quantity.*—An average of 18 (9 pairs) per stem.

Flower description:

*Inflorescence type.*—Compound cyme.

*Lastingness of inflorescence.*—Freely flowering, individual flowers lasts about 10 days, 3 to 4 weeks per inflorescence, inflorescences are continuously produced during the bloom season.

*Inflorescence size.*—An average of 4.3 cm in height, 5.1 cm in diameter.

*Flower fragrance.*—Faint, sweet and pleasant *Phlox* fragrance.

*Flower number.*—Average of 13 per inflorescence, 80 flowers per plant, 420 buds per plant.

*Flower aspect.*—All directions.

*Flower bud.*—An average of 1.4 cm in length and up to 3 mm in diameter, oblanceolate in shape, color; 92A, immature tube 93C, immature calyx 70C, base N77D, surface smooth, glabrous, matte and moderately covered with short hairs an average of 0.4 mm in length, 70C to 70D in color.

*Flower form.*—Salverform, single.

*Flower size.*—An average of 2.1 cm in height and diameter, 1.4 cm in depth, throat 1.5 mm in diameter, tube 1.2 cm in length and 1.75 mm in diameter.

*Petals.*—5, rotate, self-cleaning, both surfaces are glabrous, upper surface matte, lower surface matte and slightly velvety, petals are fused 52% into tube, spathulate in shape, margins entire, broadly mucronulate apex, average of 2.3 cm in length, 7 mm in width, color: when opening and fully upper surface; 92A, basal margins N88D, base N87B, fading to N87C, basal margins, N88D, base N87A to N87B, when opening lower surface; 91A, when fully open lower surface; 94C, fading to N87C, base N88D, flower throat; N87A, flower tube; a blend of N92A and N92D.

*Sepals.*—5, rotate, lanceolate in shape, 30% of base fused, margins entire, apex narrowly acuminate in shape, an average of 5 mm in length and 0.8 mm in width, color: when opening and fully open upper surface; 84D, when opening and fully open lower surface 70C, base 147C, surface; upper surface glabrous, matte, smooth, lower surface matte and moderately covered with short pubescent hairs an average of 0.4 mm in length, 70C to 70D in color.

*Calyx.*—Rotate, lower 20% fused, 6 mm in length, 5 mm in diameter.

*Peduncles.*—Moderately strong, oval in shape, 2.4 cm in length, 1 mm in diameter, held in a vertical angle, color; 178C, tinged N77C, surface is moderately glossy and moderately to densely covered with short pubescent hairs an average of 0.5 mm in length, N155A in color.

*Pedicels.*—Moderately strong, round in shape, 4 mm in length, 0.75 mm in diameter, held in a 45° angle, color; 197A, surface is moderately glossy and moderately to densely covered with short pubescent hairs; an average of 0.3 mm in length too small to measure color.

Reproductive organs:

*Gynoecium.*—Pistil; 1, 1.5 mm in length, stigma; cleft (3-parted), 4A in color, 1.5 mm in length, style; 0.5 mm in length, 145C in color, ovary; N144D in color.

*Androecium.*—Stamens; 5, anthers; narrow oblong in shape, 2 mm in length, 1 mm in width, 3C in color, filaments; 0.5 mm in length, N92D in color, pollen is moderate in quantity and 4A in color.

*Seeds.*—None observed to date.

It is claimed:

1. A new and distinct cultivar of *Phlox* plant named 'Blue Ribbons' as herein illustrated and described.

* * * * *